US010780197B1

(12) United States Patent
Williams et al.

(10) Patent No.: US 10,780,197 B1
(45) Date of Patent: Sep. 22, 2020

(54) MALLEABLE, CRYOPRESERVED OSTEOGENIC COMPOSITIONS WITH VIABLE CELLS

(71) Applicant: NuVasive, Inc., San Diego, CA (US)

(72) Inventors: Gregory Williams, San Diego, CA (US); Erik Erbe, San Diego, CA (US); Susan Riley, San Diego, CA (US); Timothy Moseley, Solana Beach, CA (US); Ali Ismailoglu, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 219 days.

(21) Appl. No.: 14/066,589

(22) Filed: Oct. 29, 2013

Related U.S. Application Data

(60) Provisional application No. 61/719,868, filed on Oct. 29, 2012.

(51) Int. Cl.
*A61L 27/36* (2006.01)

(52) U.S. Cl.
CPC .................. *A61L 27/365* (2013.01)

(58) Field of Classification Search
CPC ..................................................... A61L 27/365
See application file for complete search history.

(56) References Cited

U.S. PATENT DOCUMENTS

| | | |
|---|---|---|
| 4,065,816 A | 1/1978 | Sawyer |
| 4,108,161 A | 8/1978 | Samuels et al. |
| 4,802,853 A | 2/1989 | Krasner |
| 5,345,746 A | 9/1994 | Franchi |
| 5,385,229 A | 1/1995 | Bittmann et al. |
| 5,480,424 A | 1/1996 | Cox |
| 5,531,791 A | 7/1996 | Wolfinbarger, Jr. |
| 5,676,146 A | 10/1997 | Scarborough |
| 5,697,383 A | 12/1997 | Manders et al. |
| 5,910,315 A | 6/1999 | Stevenson et al. |
| 5,989,498 A | 11/1999 | Odland |
| 6,024,735 A | 2/2000 | Wolfinbarger, Jr. |
| 6,083,690 A | 7/2000 | Harris et al. |
| 6,189,537 B1 | 2/2001 | Wolfinbarger, Jr. |
| 6,203,755 B1 | 3/2001 | Odland |
| 6,254,635 B1 | 7/2001 | Schroeder et al. |
| 6,293,970 B1 | 9/2001 | Wolfinbarger, Jr. |
| 6,294,187 B1 | 9/2001 | Boyce |
| 6,311,690 B1 | 11/2001 | Jefferies |
| 6,432,436 B1 | 8/2002 | Gertzman et al. |
| 6,652,818 B1 | 11/2003 | Mills et al. |
| 6,739,112 B1 | 5/2004 | Marino |
| 7,162,850 B2 | 1/2007 | Marino |
| 7,892,724 B2 * | 2/2011 | Shimko .................. A01N 1/02 435/1.1 |
| 9,687,348 B2 * | 6/2017 | Vunjak-Novakovic |
| 2001/0039458 A1 | 11/2001 | Boyer, II et al. |
| 2002/0018796 A1 | 2/2002 | Wironen |
| 2004/0230309 A1 * | 11/2004 | DiMauro ................ A61F 2/441 623/17.12 |
| 2006/0083769 A1 | 4/2006 | Kumar et al. |
| 2006/0240064 A9 | 10/2006 | Hunter et al. |
| 2007/0260326 A1 | 11/2007 | Williams |
| 2008/0262633 A1 | 10/2008 | Williams |

FOREIGN PATENT DOCUMENTS

| | | | |
|---|---|---|---|
| WO | WO 9739104 A1 * | 10/1997 | ........... C12N 5/0663 |
| WO | WO-02/32474 A1 | 4/2002 | |
| WO | WO-2007/133451 A1 | 11/2007 | |
| WO | WO-2009/134815 A1 | 11/2009 | |

OTHER PUBLICATIONS

Ginis et al., Evaluation of bone marrow-derived mesenchymal stem cells after cryopreservation and hypothermic storage in clinically safe medium. Tissue Engineering Part C: Methods. Jan. 30, 2012;18(6):453-63.*
Bradley et al., Histologic Evaluation of a Stem Cell—Based Sinus-Augmentation Procedure, J Periodontol 2009;80:679-686. (Year: 2009).*
Alberts et al., Chapter 23 Specialized Tissues, Stem Cells and Tissue Renewal, Molecular Biology of the Cell, 5th Edition, 2008, p. 1457, Garland Science, New York, New York.
An et al., "Comparison Between Allograft Plus Demineralized Bone Matrix Versus Autograft in Anterior Cervical Fusion", Spine, 1995, 20(20):2211-2216.
Caplan, A., "What's in a Name?", Tissue Engineering, 2010, 16(8):2415-2417.
Cook et al., "In Vivo Evaluation of Demineralized Bone Matrix as a Bone Graft Substitute in Posterior Spinal Fusion", Spine, 1995, 20(8):877-886.
Gazdag et al., "Alternatives to Autogenous Bone Graft: Efficacy and Indications", J Am Acad Orthop Surg, 1995, 3(1):1-8.
Lambrecht and Marks, "Human Osteoclast-like Cells in Primary Cultures" Clinical Anatomy, 1996, 9:41-45.
Laursen et al., "Optimal handling of fresh cancellous bone graft. Different peroperative storing techniques evaluated by in vitro osteo-blast-like cell metabolism", Acta Orthop Scand, 2003, 74(4):490-496.
Meyer H., "Properties of Human Trabecular Bone Cells from Elderly Women: Implications for Cell-Based Bone Engraftment" Cells Tissues Organs, 2004, 177:57-67.
Robey et al., "Human Bone Cells In Vitro", Calcif Tissue Int, 1985, 37:453-460.
Sakaguchi et al., "Suspended cells from trabecular bone by collagenase digestion become virtually identical to mesenchymal stem cells obtained from marrow aspirates", Blood, 2004, 104(9):2728-2735.

(Continued)

*Primary Examiner* — Michael G. Hartley
*Assistant Examiner* — Nabila G Ebrahim

(57) ABSTRACT

A bone graft composition comprising a viable, osteogenic cellular material combined with a viscous cryoprotectant that includes a penetrating cryoprotective agent and a non-penetrating cryoprotective agent. The viscosity of the cryoprotectant is such that the composition is malleable, cohesive and capable of being formed into desired shapes.

16 Claims, No Drawings

(56) References Cited

OTHER PUBLICATIONS

International Search Report in International Application No. PCT/US07/10589 dated Oct. 24, 2007, 1 page.
Written Opinion of the International Searching Authority in International Application No. PCT/US07/10589 dated Oct. 24, 2007, 3 pages.
International Search Report in International Application No. PCT/US2009/041999 dated Jun. 24, 2009, 2 pages.
Written Opinion of the International Searching Authority in International Application No. PCT/US2009/041999 dated Jun. 24, 2009, 5 pages.

* cited by examiner

MALLEABLE, CRYOPRESERVED OSTEOGENIC COMPOSITIONS WITH VIABLE CELLS

CROSS REFERENCE TO RELATED APPLICATIONS

This application claims the benefit of the filing date of U.S. Provisional Patent Application No. 61/719,868 which was filed on Oct. 29, 2012. The content of U.S. Application No. 61/719,868 is incorporated by reference as part of this application.

FIELD

This application relates to a bone graft composition, useful in surgical applications, comprising viable cellular material combined with a viscous cryoprotectant.

SUMMARY

According to an exemplary embodiment, the bone graft composition comprises a viable, osteogenic cellular material combined with a viscous cryoprotectant that includes a penetrating cryoprotective agent and a non-penetrating cryoprotective agent. According to an exemplary embodiment, the viscosity of the cryoprotectant is such that the composition is malleable, cohesive and capable of being formed into desired shapes. According to another exemplary embodiment, the osteogenic cellular material includes viable mesenchymal stem cells. According to yet another embodiment, the osteogenic composition includes at least one of demineralized cortical bone, demineralized cancellous bone, growth factors, bone marrow, BMP-2, BMP-4, BMP-7, or a combination thereof. The characteristics of viscous cryoprotectant allow the composition to be frozen and subsequently thawed and implanted into a patient in need thereof while preserving the viability of the mesenchymal stem cells in the composition.

According to one aspect, the viable osteogenic cellular material is autogenous bone matrix having a population of endogenous osteopotent and/or osteogenic cells. According to another aspect, the viable osteogenic cellular material is allogeneic bone matrix having a population of endogenous osteopotent and/or osteogenic cells. The viable osteogenic cellular material may be substantially depleted of blood cells. The cellular material may include mesenchymal stem cells derived from bone marrow, adipose tissue, muscle, synovium, synovial fluid, dental pulp and/or umbilical cord origin.

According to another aspect, non-penetrating cryoprotective agent is one of alginate, hyaluronic acid, hydroxyethyl starch, methylcellulose, carboxymethylcellulose, hydroxymethylcellulose, polyvinylpyrrolidone, polyethylene glycol, chitosan, glycerol, or a combination thereof. The penetrating cryoprotective agent is one of dimethyl sulfoxide, glycerol, propylene glycol, ethylene glycol, propanediol, or a combination thereof.

According to another exemplary embodiment, the bone graft composition further comprises a scaffold material. For example, the scaffold material is one of non-demineralized, partially demineralized and demineralized cortical bone matrix; nondemineralized, partially demineralized and demineralized cancellous bone matrix; hydroxyapatite, tricalcium phosphate, calcium sulfate, collagen or a combination thereof.

According to yet another exemplary embodiment, the viable osteogenic cellular material comprises particles cohesively bound by the viscous cryoprotectant. Alternatively, the viable osteogenic cellular material may be coated or encapsulated by the viscous cryoprotectant.

DETAILED DESCRIPTION

Aspects of the invention are disclosed in the following description. Alternate embodiments may be devised without departing from the spirit or the scope of the invention. Additionally, well-known elements of the invention will not be described in detail or omitted so as not to obscure the relevant details of the invention.

Example 1

Viscous cryoprotectant compositions were created for subsequent combination with tissue components. A 10% (v/v) dimethyl sulfoxide (DMSO) solution was created in an isotonic, pH neutral solution with acetate and gluconate buffers. Pre-weighed quantities of sodium alginate were dissolved in the 10% DMSO solution to achieve concentrations of 1%-4% (w/v) alginate. Alginates had been pre-selected with a Brookfield viscosity specification in the range of 100-10,000 cps when tested at 2% in water at 25 degrees C.

Relative apparent viscosities were determined for each of the final cryoprotectant solutions and ranked such that 7>6>5>4>3>2>1, as shown in Table 1.

TABLE 1

| Cryoprotectant Solution ID | Alginate Concentration | Alginate Viscosity Spec | Relative Viscosity |
| --- | --- | --- | --- |
| A | 1% | 100-300 cps | 1 |
| B | 2% | 100-300 cps | 2 |
| C | 4% | 100-300 cps | 5 |
| D | 1% | >2000 cps | 3 |
| E | 1.5% | >2000 cps | 4 |
| F | 2% | >2000 cps | 6 |
| G | 4% | >2000 cps | 7 |

Example 2

Viable cellular cancellous bone was ground and sieved to 425-2000 μm. Cortical bone was ground, sieved to 125-1000 μm, and demineralized to <8% residual calcium content to create hydrated demineralized bone matrix (DBM). Tissue components were mixed in cancellous:DBM volume ratios of 10:3-2:1. Tissue mixtures were combined with cryoprotectants essentially identical to those of Example 1 at a cancellous:cryoprotectant volume ratio of 5:1. Tissue and cryoprotectant components were mixed to form malleable compositions with variously satisfactory cohesiveness and formability, as shown in Table 2.

TABLE 2

| Cancellous:DBM (v:v) | Cryoprotectant Solution ID | Cancellous:Cryo (v:v) | Cohesiveness/Formability |
| --- | --- | --- | --- |
| 10:3 | D | 5:1 | poor |
| 10:3 | E | 5:1 | poor |
| 10:3 | C | 5:1 | fair |
| 10:3 | F | 5:1 | fair |

TABLE 2-continued

| Cancellous:DBM (v:v) | Cryoprotectant Solution ID | Cancellous:Cryo (v:v) | Cohesiveness/ Formability |
|---|---|---|---|
| 2:1 | F | 5:1 | fair |
| 2:1 | G | 5:1 | good |

Example 3

Viable cellular cancellous bone was ground and sieved to 425-2000 μm. Cortical bone was ground, sieved to 100-710 μm, demineralized to <8% residual calcium content, and lyophilized to create lyophilized DBM. Tissue components were mixed at a cancellous:DBM volume ratio of 2:1. The tissue mixture was combined with cryoprotectants essentially identical to those of Example 1 at cancellous:cryoprotectant volume ratios of 10:3-5:2. Tissue and cryoprotectant components were mixed and evaluated for cohesiveness and formability; the results are summarized in Table 3.

TABLE 3

| Cancellous:DBM (v:v) | Cryoprotectant Solution ID | Cancellous:Cryo (v:v) | Cohesiveness/ Formability |
|---|---|---|---|
| 2:1 | G | 10:3 | fair |
| 2:1 | G | 5:2 | good |

Example 4

Viable cellular cancellous bone was ground and sieved to 425-2000 μm. Cortical bone was ground, sieved to 100-710 μm, demineralized to <8% residual calcium content, and lyophilized to create lyophilized DBM. Lyophilized DBM was subsequently rehydrated in an isotonic, neutral pH solution and mixed with cancellous bone at a cancellous:DBM volume ratio of 10:7. The tissue mixture was combined with a cryoprotectant essentially identical to Solution G in Example 1 at a cancellous:cryoprotectant volume ratio of 10:3. Tissue and cryoprotectant components were mixed and evaluated for cohesiveness and formability; the results are summarized in Table 4.

TABLE 4

| Cancellous:DBM (v:v) | Cryoprotectant Solution ID | Cancellous:Cryo (v:v) | Cohesiveness/ Formability |
|---|---|---|---|
| 10:7 | G | 10:3 | good |

Example 5

Viscous cryoprotectant compositions were created for subsequent combination with tissue components. Pre-weighed quantities of sodium alginate having a Brookfield viscosity specification of >2000 cps when tested at 2% in water at 25 degrees C. were suspended in measured volumes of DMSO. Measured quantities of an isotonic, pH neutral solution with acetate and gluconate buffers were mixed with the alginate/DMSO suspensions to create substantially homogeneous cryoprotectant solutions with final DMSO concentrations of 5%-10% (v/v) and alginate concentrations of 2%-4% (w/v).

Relative apparent viscosities were determined for each of the final cryoprotectant solutions and ranked such that 7>6>5>4>3>2>1, as shown in Table 5.

TABLE 5

| Cryoprotectant Solution ID | Alginate Concentration | DMSO Concentration | Relative Viscosity |
|---|---|---|---|
| H | 2% | 5% | 1 |
| I | 2.5% | 5% | 2 |
| J | 3% | 5% | 4 |
| K | 4% | 5% | 6 |
| L | 2% | 10% | 3 |
| M | 2.5% | 10% | 5 |
| N | 3% | 10% | 6 |
| O | 4% | 10% | 7 |

Example 6

Viable cellular cancellous bone was ground and sieved to 425-2000 μm. Cortical bone was ground, sieved to 125-1000 μm, and demineralized to <8% residual calcium content to create hydrated DBM. Tissue components were mixed at cancellous:DBM volume ratios of 5:1-2:1. Tissue mixtures were combined with a cryoprotectant essentially identical to Solution 0 of Example 5 with the addition of 2% (w/v) human serum albumin at cancellous:cryoprotectant volume ratios of 5:1-4:1. Tissue and cryoprotectant components were mixed and evaluated for cohesiveness and formability, the results of which are summarized in Table 6.

TABLE 6

| Cancellous:DBM (v:v) | Cancellous:Cryo (v:v) | Cohesiveness/ Formability |
|---|---|---|
| 5:1 | 5:1 | fair |
| 4:1 | 5:1 | fair |
| 3:1 | 5:1 | good |
| 2:1 | 5:1 | good |
| 5:1 | 4:1 | fair |
| 4:1 | 4:1 | fair |
| 3:1 | 4:1 | good |
| 2:1 | 4:1 | better |

Example 7

Viable cellular cancellous bone was ground and sieved to 425-2000 μm. Cortical bone was ground, sieved to 125-1000 μm, and demineralized to <8% residual calcium content to create hydrated DBM. Tissue components were mixed at a cancellous:DBM volume ratio of 2:1. Cryoprotectant solutions were created consisting of DMSO at 5%-10% (v/v), human serum albumin at 0%-2% (w/v), and alginate at 4% (w/v) in an isotonic, neutral pH parenteral solution. Tissue mixtures were combined with cryoprotectants at a cancellous:cryoprotectant volume ratio of 4:1. Tissue and cryoprotectant components were mixed to create substantially homogeneous malleable compositions. Compositions were frozen to −80±5° C. to cryopreserve tissue components and viable cells.

Compositions were subsequently thawed and tested for cell viability (% viable cells) and cell concentrations (cells per cc of tissue). Compositions were rinsed immediately after thawing with phosphate buffered saline to dilute and decant the viscous cryoprotectant solutions. The remaining tissue components were treated with 3 mg/ml collagenase in phosphate buffered saline at 37° C. to release cells off bone matrix for counting. Released cells were washed and resuspended in Dulbecco's Modified Eagle Medium with 10% fetal bovine serum and then stained with Trypan blue. Live (negative staining) and dead (positive staining) cells were counted with the aid of a hemocytometer and microscope. The results are summarized in Table 7.

TABLE 7

| Composition ID | DMSO Concentration (v/v) | Human Serum Albumin Concentration (w/v) | Avg. Cell Viability | Avg. Cell Count (cells/cc) |
| --- | --- | --- | --- | --- |
| A | 10% | 0% | 76.4% | 4,154,500 |
| B | 7.5% | 0% | 74.7% | 3,787,000 |
| C | 5% | 0% | 77.2% | 4,399,500 |
| D | 10% | 2% | 76.8% | 4,301,500 |
| E | 7.5% | 2% | 80.6% | 4,063,500 |
| F | 5% | 2% | 77.1% | 3,279,500 |

Example 8

Viable cellular cancellous bone was ground and sieved to 425-2000 μm. Cortical bone was ground, sieved to 125-1000 μm, and demineralized to <8% residual calcium content to create hydrated DBM. Tissue components were mixed at cancellous:DBM volume ratios of 5:2 to 5:3. Cryoprotectant solutions were created consisting of DMSO at 10% (v/v), human serum albumin at 2% (w/v), and alginate at 6% (w/v) in an isotonic, neutral pH parenteral solution. Alginates in this example had molecular weights (MW) between 50,000 and 150,000 g/mol. Tissue mixtures were combined with cryoprotectants at cancellous:cryoprotectant volume ratios of 5:2 to 2:1. Tissue and cryoprotectant components were mixed to create substantially homogeneous malleable compositions. Compositions were frozen to −80±5° C. to cryopreserve tissue components and viable cells.

Compositions were subsequently thawed and tested for cell viability (% viable cells), cell concentrations (cells per cc of tissue), and osteogenic potential. Compositions were rinsed immediately after thawing with phosphate buffered saline to dilute and decant the viscous cryoprotectant solutions. The remaining tissue components were treated with 3 mg/ml collagenase in phosphate buffered saline at 37° C. to release cells off bone matrix for counting. Released cells were washed and resuspended in Dulbecco's Modified Eagle Medium with 10% fetal bovine serum and then stained with Trypan blue. Live (negative staining) and dead (positive staining) cells were counted with the aid of a hemocytometer and microscope. Cells were plated and cultured in expansion medium through one passage. Cells were then switched into osteogenic medium and subsequently stained for the presence of the bone mineralization marker alkaline phosphatase. The results are summarized in Table 8.

TABLE 8

| Composition ID | Alginate Lot ID | Cancellous:Cryo (v:v) | Avg. Cell Viability | Avg. Cell Count (cells/cc) | Alk. Phos. Staining |
| --- | --- | --- | --- | --- | --- |
| A | 1 | 5:2 | 85.5% | 2,761,500 | Positive |
| B | 1 | 2:1 | 86.3% | 2,732,750 | Positive |
| C | 2 | 5:2 | 87.8% | 2,824,750 | Positive |
| D | 2 | 2:1 | 89.0% | 2,767,000 | Positive |

What is claimed is:

1. A bone graft composition comprising:
   an allograft bone scaffold including viable osteogenic cells native to the bone scaffold;
   an allograft demineralized bone matrix, wherein ratio of the bone scaffold to the allograft demineralized bone matrix ranges from 5:2 to 5:3; and
   a viscous cryoprotectant, wherein the bone scaffold to the viscous cryoprotectant ratio ranges from 5:2 to 2:1;
   wherein said viscous cryoprotectant includes at least one penetrating cryoprotective agent and at least one non-penetrating cryoprotective agent and wherein at least seventy percent (70%) of the viable osteogenic cells are viable after storage in the cryopreservative at −80 degrees Celsius (−80 C) or lower for a period of fourteen (14) days.

2. The bone graft composition of claim 1, wherein the bone scaffold further comprises a population of endogenous osteopotent cells.

3. The bone graft composition of claim 2, wherein the bone scaffold is substantially depleted of blood cells.

4. The bone graft composition of claim 1, wherein the viable osteogenic cells include mesenchymal stem cells.

5. The bone graft composition of claim 1, wherein the bone graft composition further comprising at least one of allograft non-demineralized, partially demineralized and demineralized cortical bone matrix; and at least one of allograft non-demineralized, partially demineralized and demineralized cancellous bone matrix.

6. The bone graft composition of claim 1, further comprising an osteoinductive material.

7. The bone graft composition of claim 6, wherein the osteoinductive material is at least one of demineralized cortical bone, demineralized cancellous bone, growth factors, bone marrow, BMP-2, BMP-4, BMP-7 or a combination thereof.

8. The bone graft composition of claim 1, wherein the non-penetrating cryoprotective agent is one of alginate, hyaluronic acid, hydroxyethyl starch, methylcellulose, carboxymethylcellulose, hydroxymethylcellulose, polyvinylpyrrolidone, polyethylene glycol, chitosan, glycerol, or a combination thereof.

9. The bone graft composition of claim 1, wherein the penetrating cryoprotective agent is one of dimethyl sulfoxide, glycerol, propylene glycol, ethylene glycol, propanediol, or a combination thereof.

10. A method of preserving the viability during freezing of a bone graft material comprising
    combining bone graft material with a viscous cryoprotectant, wherein the bone graft material to viscous cryoprotectant ratio ranges from 5:2 to 2:1; combining the bone graft material with an allograft demineralized bone matrix, wherein ratio of the bone scaffold to the allograft demineralized bone matrix ranges from 5:2 to 5:3; and wherein (i) the viscous cryoprotectant includes at least one non-penetrating cryoprotective agent and at least one penetrating cryoprotective agent and (ii) at least seventy percent (70%) of the bone graft material is viable after storage in the cryopreservative at −80 degrees Celsius (−80 C) or lower for a period of fourteen (14) days, wherein the bone graft material comprises an allograft bone scaffold including viable, native osteogenic cells.

11. The bone graft composition of claim 1, wherein the bone scaffold comprises particles cohesively bound by the viscous cryoprotectant.

12. The bone graft composition of claim 1, wherein the bone scaffold is coated by the viscous cryoprotectant.

13. The bone graft composition of claim 1, wherein
the allograft bone matrix is from viable cancellous bone, and wherein the allograft bone scaffold is obtained from viable cortical bone, or the allograft bone matrix is obtained from the viable cortical bone, and wherein the allograft bone scaffold is obtained from the viable cancellous bone.

14. The method of claim 10, wherein the
allograft bone matrix is from viable cancellous bone, and wherein the allograft bone scaffold is obtained from viable cortical bone, or the allograft bone matrix is obtained from the viable cortical bone, and wherein the allograft bone scaffold is obtained from the viable cancellous bone.

15. The bone graft composition of claim 1, wherein the allograft bone scaffold is cohesively bound, coated, or encapsulated by the viscous cryoprotectant.

16. The bone graft composition of claim 1, wherein a viscosity of the cryoprotectant is higher than 2000 centipoises (cps).

\* \* \* \* \*